United States Patent [19]

Bauer

[11] Patent Number: 5,014,722
[45] Date of Patent: May 14, 1991

[54] INTRA-UTERINE PESSARY

[76] Inventor: Hans A. Bauer, Marquardsenstrasse 8, D-8520 Erlangen, Fed. Rep. of Germany

[21] Appl. No.: 445,691
[22] PCT Filed: Mar. 17, 1989
[86] PCT No.: PCT/DE89/00171
§ 371 Date: Nov. 17, 1989
§ 102(e) Date: Nov. 17, 1989
[87] PCT Pub. No.: WO89/09038
PCT Pub. Date: Oct. 5, 1989

[30] Foreign Application Priority Data

Mar. 30, 1988 [DE] Fed. Rep. of Germany ....... 3810925
Mar. 1, 1989 [DE] Fed. Rep. of Germany ....... 3906377

[51] Int. Cl.$^5$ ............................ A61F 6/06; A61F 6/14
[52] U.S. Cl. ...................................... 128/830; 128/839
[58] Field of Search ................................ 128/830-841

[56] References Cited

U.S. PATENT DOCUMENTS

| 1,896,071 | 2/1933 | Clark | 128/839 |
| 3,323,520 | 6/1967 | Hall | 128/839 |
| 3,431,906 | 3/1969 | Taylor | 128/839 |
| 3,490,446 | 1/1970 | Slonek | 128/839 |
| 3,492,990 | 2/1970 | Clarke | 128/840 |
| 3,507,274 | 4/1970 | Soichet | 128/840 |
| 3,515,132 | 6/1970 | McKnight | 128/840 |
| 3,516,403 | 6/1970 | Cournut | 128/840 |
| 3,678,927 | 7/1972 | Soichet | 128/840 |
| 3,913,573 | 10/1975 | Gutnick | 128/839 |
| 4,005,707 | 2/1977 | Moulding, Jr. | 128/839 |
| 4,038,978 | 8/1977 | Morris | 128/840 |
| 4,054,131 | 10/1977 | Kessel | 128/839 |
| 4,246,896 | 1/1981 | Horne, Jr. | 128/840 |
| 4,690,136 | 9/1987 | van Os | 128/840 |
| 4,724,832 | 2/1988 | Strubel | 128/840 |

FOREIGN PATENT DOCUMENTS 0214172 3/1909 Fed. Rep. of Germany .
0981389 6/1963 United Kingdom .

Primary Examiner—Robert A. Hafer
Assistant Examiner—Michael Brown
Attorney, Agent, or Firm—Toren, McGeady & Associates

[57] ABSTRACT

An intra-uterine pessary includes two spreading arms which are in a folded configuration for insertion through the cervical canal and assume an unfolded configuration for retention in the uterine cavity. The two spreading arms form a substantially closed-loop structure in the folded and in the unfolded configuration. The spreading arms are traversed by a third arm which is connected to the spreading arms and to an abutment mounted on the spreading arms. The length of the third arm is changeable. The two spreading arms are made exclusively of a metal wire and are straightened in the folded configuration and have an annular shape and are elastically bent in the unfolded configuration. The length of the third arm can be finely adjustably controlled when the spreading arms ae in the unfolded configuration.

7 Claims, 1 Drawing Sheet

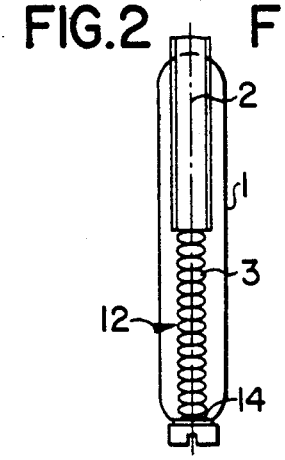
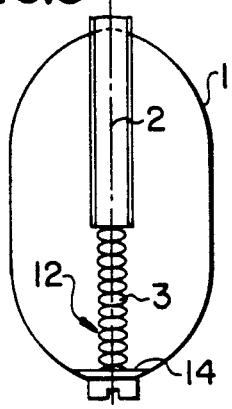
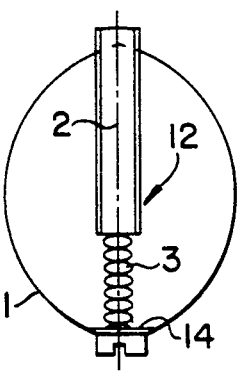
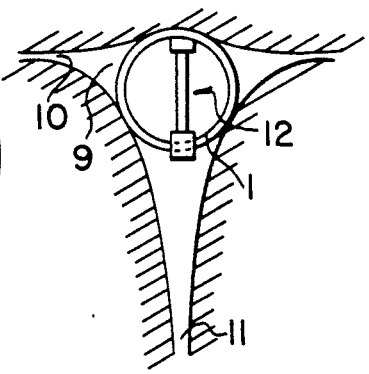
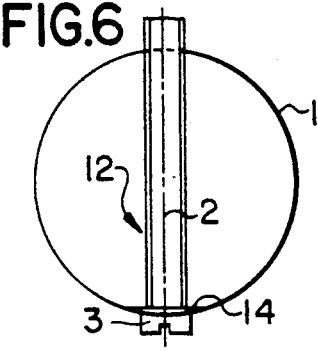
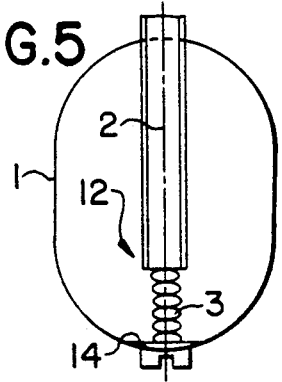
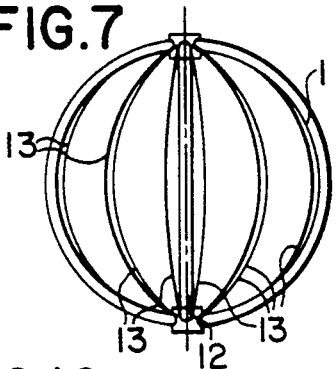
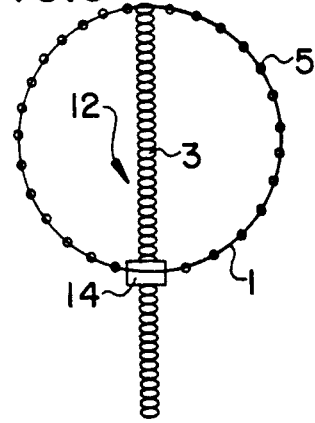
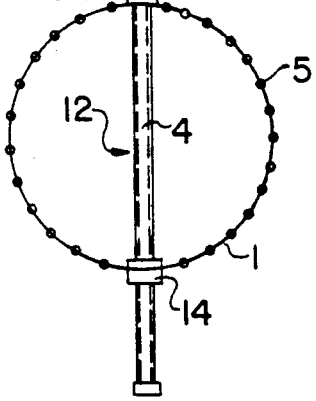
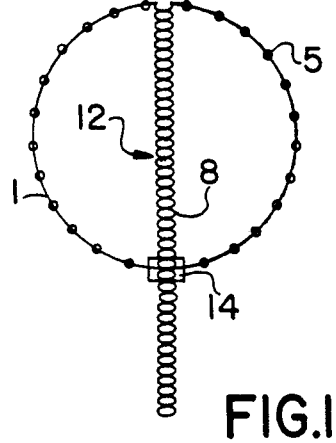
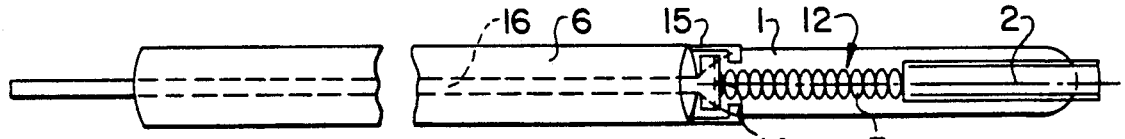
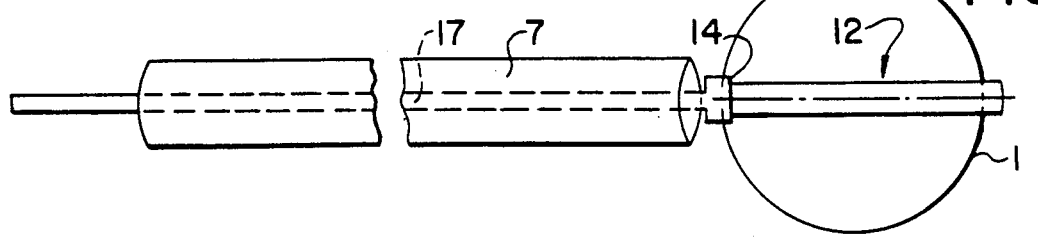

INTRA-UTERINE PESSARY

DESCRIPTION

This invention relates to an intra-uterine contraceptive pessary having parts emitting ions in the uterine cavity and having two spreading arms which are in a straightened out configuration for insertion through the cervical canal into the uterine cavity and which assume an annular configuration for retention in the uterine cavity and which for the purpose of insertion in the straightened configuration and spreading into the annular configuration comprises means for resilient bending of the spreading arms.

In a prior-art (U.S. Pat. No. 40 18 220) intra-uterine pessary of this kind, the two spreading arms form a structure which is open at one point both in the straightened configuration and in the annular configuration. The spreading arms are premoulded into a partly circular bowed shape, consist of plastic and are elastically deformed when straightened out so that on being extended, that is when spreading into an annular configuration, will return into their original shape due to this resilience. Both the use of plastic for the spreading arms and the open configuration, i.e. the free ends of the spreading arms, are liable to be a source of trouble when the intra-uterine pessary is used for an extended period of time. The spread of the arms when in the annular configuration is predetermined so that the intra-uterine pessary will have to be available in many different sizes in order to maintain a good fit in view of the varying width of the uterine cavity.

It is an object of the present invention to provide an intra-uterine pessary of the type initially referred to whose spread can be finely adjusted or controlled while avoiding plastic as a material of the spreading arms and avoiding an open spreading arm configuration. In solving this problem, the intra-uterine pessary according to the invention is characterized in that the spreading arms form a substantially closed structure both in the straightened configuration and in the annular configuration, a third arm extending transversely through the structure engaging at one end the spreading arms and, at the other end, an abutment closure joining the spreading arms and which is adapted to be shortened under mechanical control to change from the straightened configuration to the annular configuration for spreading the device and in that the two spreading arms are formed by metal wire adapted to be deformable elastically during spreading and the abutment closure is located at the spreading arms.

The invention provides an intra-uterine contraceptive pessary whose spread or opening width is controlled to adapt to the specific width of the uterine cavity. The closed annular shape may be longitudinally oval in the direction of the third arm, circular or transversely oval in a direction transverse to the third arm. This closed annular shape unfolds on insertion of the intra-uterine pessary through the cervical canal under mechanical control by means of the third arm which is variable in length in fine steps or steplessly. In the process, the spreading arms assume the desired curved shape and the abutment closure lies outside the cervical canal also within the uterine cavity. The intra-uterine pessary is capable of being controlled to assume an insertion shape and a retention shape which differ from each other.

It is specially desirable and advantageous if the intra-uterine pessary is purely metallic. This can be achieved relatively easily because no plastic need be used for the spreading arms.

In the straightened configuration or substantially straight shape for insertion, the intra-uterine pessary according to the invention is similar to a safety pin having a third arm added which is adapted to be shortened and extends in parallel with the two straightened spreading arms. As the third arm is shortened, the spreading arms are displaced or bowed outwardly by an amount which is variable.

It is specially desirable and advantageous if the third arm comprises a threaded member which is rotatable in a mating thread, e.g. in the abutment closure. Turning of the threaded member will permit the length of the third arm to be steplessly varied. The third arm may consist of a single part or a plurality of parts.

Furthermore, it is specially desirable and advantageous if the third arm comprises a chain or tension wire which is adapted to be secured to an opposing bearing in the abutment closure for length adjustment. This permits stepless or finely graded variation of the length of the third arm. The third arm in this case may also consist of a single part or a plurality of parts.

Furthermore, it is specially desirable and advantageous if, in addition to the two spreading arms, thinner secondary arms made of metal wire are spaced on the circumference around the third arm. This intra-uterine pessary can be extended from the straight (collapsed) shape into a spherical shape or the shape of a mirror-image umbrella structure wherein the thinner secondary arms extend in a meridional direction. After resilient and plastic deformation, the secondary arms will rest against the anterior and posterior walls of the uterine cavity.

An insertion instrument is associated with the intra-uterine pessary according to the invention wherein a manipulating rod is arranged in a hollow tube. For the purpose of spreading the device, provision is made for the manipulating rod to engage the third arm and for the hollow tube to bear against the spreading arms. In this manner, the shortening of the third arm relative to the spreading arms can be effected from outside the uterine cavity.

In one embodiment of the invention, the original "guard end of the safety pin" is replaced by a second spring region with or without a spring spiral or spring coils, this spring region joining the spreading arms into a closed loop. A spring spiral or spring coil, if provided, may, for instance, be placed at an angle or slant relative to the spreading arms, e.g., offset 90 degrees. The supporting structure, that is the third arm, the spreading arms and the secondary arms, if provided, may consist of only one metal or a plurality of different metals. The metals may, for instance, be bonded for electric conductance or insulated against each other by means of a metallic oxide dielectric or bonded for poor conductance. The complete supporting structure of the intra-uterine pessary may in one embodiment be strung or provided with a plurality of localized parts consisting of ion-emitting metals, their connection to the supporting structure being either electrically conducting or non-conducting or poorly conducting.

The hollow tube of the insertion instrument is of a roundish shape and provided with a terminal holding device for the intra-uterine pessary. Removal of the intra-uterine pessary is effected either in the reverse order of the insertion operation or by pulling the intra-uterine pessary into the hollow tube to be removed with the latter. The ion-emitting parts consist of suitable metals, such as copper or zinc. The desired spread can be read off a calibration scale on the insertion instrument. The spreading arms may have a wavy shape with convex and concave sections which improve resistance of the intra-uterine pessary to expression. A thin metal pilot chain may be provided on the intra-uterine pessary which extends in the direction towards the external os of the uterus.

Preferred embodiments of the invention are illustrated in the drawing in which:

FIG. 1 shows an intra-uterine pessary in a uterine cavity,

FIGS. 2-6 show the intra-uterine pessary according to FIG. 1 in different stages of unfolding, FIG. 7 is a perspective view of an intra-uterine pessary with secondary arms, FIG. 8 shows an intra-uterine pessary with a threaded rod, FIGS. 9 and 10 each show an intra-uterine pessary with a chain, FIG. 11 shows an insertion instrument with the intra-uterine pessary according to FIG. 2 in the straightened out configuration and FIG. 12 an instrument similar to FIG. 11 with the intra-uterine pessary in the annular configuration.

Referring to FIG. 1, an intra-uterine pessary lies in a uterine cavity 9 which widens upwardly and continues into the two Fallopean ducts 10 at the sides. The uterine cavity 9 tapers downwards into the cervical canal 11. The intra-uterine pessary is of circular shape and contacts the two lateral walls of the uterine cavity 9 as well as the top transverse wall. The intra-uterine pessary comprises two equally formed spreading arms 1 which are shown straightened in FIG. 2 and have both ends joined to form a closed loop. Between the two spreading arms 1 there is a third arm 12 extending across and engaging the two junctions which form the spreading arms 1 into a closed loop.

FIG. 2, the third arm 12 comprises a tubular sleeve 2 with an internal thread for varying its length, the tubular sleeve being solidly connected to the junction which forms the spreading arms 1 into a closed loop at the top. Screwed a short distance into the tubular sleeve 2 is a threaded rod 3 formed as a screw which is held at a point close to the screw head at the second junction forming the spreading arms 1 into a closed loop at the bottom in a manner permitting rotation, but axially non-slidably in an abutment closure 14. As shown in FIGS. 3-6, the threaded rod 3 is screwed in further into the threaded sleeve 2 until it is at the maximum depth in FIG. 6 and the spreading arms 1 have assumed a semi-circular shape. The third arm 12 composed of the tubular sleeve 2 and the threaded rod 3 may consist, for instance, of copper and, consequently, is a member emitting ions in the uterine cavity.

The intra-uterine pessary according to FIG. 7 is formed with a group of three additional secondary arms 13 of thinner cross-section on each side of the plane in which lie the two spreading arms 1, these secondary arms being also bowed to a semi-circular shape when spread for retention. According to FIG. 8-10, parts 5 formed as small beads are provided on the spreading arms these beads consisting of an ion-emitting metal. The parts 5 are provided in series along the wire-like spreading arms 1. According to FIG. 8, the third arm 12 is formed as a relatively long threaded rod 4 which is secured rotatably at the top closing junction and, at the bottom closing junction of the spreading arms 1 penetrates through a bore provided with an internal mating thread in an abutment closure 14. According to FIGS. 9 and 10, the third arm 12 is formed as a thin chain 8 which penetrates through a chain lock formed in the abutment closure 14, this chain lock comprising a keyhole-shaped opening whose wider part permits the chain to pass through and whose narrow opening retains the chain. FIGS. 9 and 10 differ in the method of attaching the chain 8 at the top closing junction of the spreading arms 1.

The insertion instrument shown in FIG. 11 comprises a hollow tube 6 which, at one end, has a holding device 15 which engages the spreading arms 1 and secures the intra-uterine pessary against rotary forces during spreading. Provided inside the hollow tube 6 is a manipulating rod 16 formed as a key engaging the screw head of the threaded rod 3. As shown in FIG. 12, the spread intra-uterine pessary is engaged with a manipulating rod 17 at the third arm 12 and pulled into a tube 7, the two spreading arms 1 being squeezed together in the direction towards the third arm 12.

I claim:

1. In an intra-uterine contraceptive pessary having pats emitting ions in the uterine cavity, the pessary including two spreading arms which are in a folded configuration for insertion through the cervical canal and which assume an unfolded configuration for retention in the uterine cavity, wherein a change from the folded configuration into the unfolded configuration comprises an elastic deformation of the spreading arms, wherein the two spreading arms (1) form a substantially closed-loop structure in the folded configuration and in the unfolded configuration, the two spreading arms (1) being traversed by a third arm (12) which, at its one end, engages the spreading arms (1) and, at its other end, an abutment (14) mounted on the spreading arms, wherein for the purpose of changing the spreading arms (1) from the folded configuration into the unfolded configuration for retention, the length of the third arm is capable of being mechanically changed, wherein the improvement comprises that the two spreading arms (1) consist exclusively of a metal wire, the spreading arms (1) being straightened in the folded configuration and having an annular shape and being elastically bent in the unfolded configuration, the abutment (14) being a closure to which the third arm (12) is connected, further comprising means for finely controllably adjusting the length of the third arm (12) between the two ends acting on the spreading arms (1) with the spreading arms (1) being in the unfolded configuration.

2. Intra-uterine pessary as in claim 1, characterized in that it is of purely metallic construction.

3. Intra-uterine pessary as in claim 1, characterized in that the third arm (12) comprises for changing the length thereof a threaded rod (3,4) which is rotatable in a mating thread and acts as the closure.

4. Intra-uterine pessary as in claim 1, characterized in that the third arm (12) comprises a flexible oblong member which is arrestable for length adjustment in a counter-bearing in the abutment closure (14).

5. Intra-uterine pessary as in claim 4, wherein the flexible oblong member is a chain.

6. Intra-uterine pessary as in claim 4, wherein the flexible oblong member is a tension wire.

7. Intra-uterine pessary as in claim 1, characterized in that, in addition to the two spreading arms (1) thinner secondary arms (13) made of metallic wire are spaced on a circumferential line around the third arm (12).

* * * * *